US005650372A

United States Patent [19]

Branly et al.

[11] Patent Number: 5,650,372

[45] Date of Patent: Jul. 22, 1997

[54] PLANT TREATMENT WITH BACILLUS STRAIN ATCC

[75] Inventors: Keith L. Branly, Brandon; Rhett R. Atkins, Plant City, both of Fla.

[73] Assignee: Micro Flo Company, Mulberry, Fla.

[21] Appl. No.: 453,683

[22] Filed: May 30, 1995

[51] Int. Cl.$^6$ .................... A01N 63/00

[52] U.S. Cl. .................... 504/117; 424/405; 435/252.5; 435/834; 435/839

[58] Field of Search .................... 504/117; 424/405; 435/252.5, 834, 839

[56] References Cited

U.S. PATENT DOCUMENTS

| | | | |
|---|---|---|---|
| 4,161,397 | 7/1979 | Bellet et al. | 71/7 |
| 5,215,747 | 6/1993 | Hairston et al. | 424/93 |
| 5,403,583 | 4/1995 | Liu et al. | 424/93.46 |

OTHER PUBLICATIONS

Owathmey et al., "Pix Effects on Earliness and Fruit Retention of Contrasting Cotton Varieties", abstract, 1994 Beltwide Cotton Conference.

Oosterhuis, "Effects of PGR-IV on the Growth and Yield of Cotton: A Review", Proc. 1994 Worldwide Cotton Conf. (Feb. 1994).

Oosterhuis et al., "Research on Plant Growth Regulators in Cotton—Summary of 1994 Results", 1995 Beltwide Cotton Conf.

US EPA, Kodiak HB label 1994.

US EPA, Pesticide Fact Sheet—*Bacillus subtilis* GB03 1992.

Utkhede et al. "Promotion of Apple Tree Growth . . . " *Can. J. Microbiol.* 38:1270–1273. 1992.

Utkhede et al. "Evaluation of monoammonium phosphate . . . " *Plant and Soil* 157:115–120. 1993. Abstract.

*Primary Examiner*—S. Mark Clardy
*Attorney, Agent, or Firm*—Banner & Witcoff, Ltd.

[57] ABSTRACT

An agriculturally effective active ingredient is applied to plant foliage before, after, or simultaneously with a transport enhancer consisting essentially of *B. cereus.* ATCC 55675, originally identified as a *B. subtilis* strain.

18 Claims, No Drawings

PLANT TREATMENT WITH BACILLUS STRAIN ATCC

FIELD OF THE INVENTION

The invention relates to the treatment of plants by a composition containing *bacillus subtilis*.

BACKGROUND OF THE INVENTION

Agricultural chemical manufacturers are always looking for ways to improve the efficacy of active ingredients used on plants. This is particularly true where the applied material is a plant growth regulator or systemic agent (e.g., insecticide, fungicide, or herbicide). Transport mechanisms into the plant and translocation among the various plant tissues is important and, in some instances, may be the primary factor determining the efficacy of the applied ingredient.

It would be useful to have a means for increasing the uptake of agriculturally active ingredients into plants. It would be particularly helpful to have such a means for plant growth regulating agents and active ingredients operating systemically in plants.

Mepiquat chloride is one chemical in particular where plant uptake and transport is important. Mepiquat chloride (N,N-dimethylpiperidinium chloride) is used annually as the active ingredient for controlling excessive vegetative growth and increasing fruit retention on millions of acres of cotton with some uses on potatoes, sweet potatoes, peanuts, grapes, corn, wheat, citrus, tomatoes, and onions. The growth stunting effects are particularly desired when the crop is grown in fertile soil or after weather conditions that favor plant growth rather than fruit production.

Cotton is a representative plant for describing the uses and effects of mepiquat chloride. Mepiquat chloride has the effect on cotton plants of stunting vegetative growth thereby forcing the plant to redirect its energies into fruit (cotton boll) production. With appropriate application of mepiquat chloride to plants that are beginning to exhibit excessive vegetative growth, cotton plant yields can be maintained or increased without harm to the plant.

Cotton plants have a predictable life cycle and growth period. Cotton plants emerge 7–10 days after the seeds are planted in a furrow. The cotton plant exhibits growth of a root system and the extension of plant height through stem and branch growth in a pattern referred to as "vegetative growth" until about the 4th–8th node. Thereafter, the plant produces a reproductive branch (the "1st fruiting site"), and all subsequent branches are reproductive. Cotton growers attempt to control the growth of the plant to ensure that the ratio of vegetative growth to reproductive growth (boll production) favors the desired range of reproductive growth.

Cotton growers generally prefer to see about 2 inches (5 cm) between main stem nodes. This ratio represents a balance between too much reproductive growth (boll production) which can cause the plant growth to outpace the rate of vegetative growth and terminate before the yield is maximized, and too much vegetative growth which reduces the number of mature bolls.

Cotton plants that have directed the majority of the available plant energy to vegetative growth are referred to as "rank" cotton and produce less bolls which mature later and are vulnerable to weather extremes for longer periods of time. Cotton that exhibits signs of going rank are readily visible by abnormal plant height relative to the boll loads and number of reproductive main stem nodes. Mepiquat chloride is used to stop cotton from going rank by modifying the cotton plant's growth characteristics.

The branches off the main stem generally always extend from alternating sides of the stem. Each branch site is called a "node" with 5–7 nodes being formed above the cotyledon leaves before the first fruit bearing branch with true leaves is formed. Node counting starts at the bottom of the plant and extends up the main stem. The "internode length" is the distance between branch sites with a new node being formed roughly every three days. For purposes of measurement and comparison, the number of nodes and internode length above node 8 are generally used to eliminate interplant fruiting node variations because fruit bearing branches will necessarily have been formed by node 8. The counting of fruiting nodes thus conventionally starts from the first reproductive node, usually no. 7 or no. 8.

Fruiting sites in cotton are referred to as "squares." Each fruit bearing branch will form 1–6, normally about 3, fruiting sites ("squares") with approximately six days between square formations on each branch. New squares and the beginning of reproductive growth in cotton plants are referred to as "pinhead" squares due to their barely visible size. After about 5–10 days, the square has grown to about the size of a match head and is a period in the plant cycle referred to as a "match head square." The match head square continues to grow to about the size of an average adult fingernail before blooming ("early bloom"). Three days later, a boll has formed beneath the bloom. Roughly thirty days after early bloom, the product boll is fully mature and ready for harvest. Overall, about 80% of the total cotton yield is set within the first 3 weeks after early bloom and 95% of the total yield is set within 5 weeks of early bloom.

Generally, mepiquat chloride is applied to cotton plants in one of two ways. The method used until about 1986 was a single application of 8–16 ounces per acre of a 4.2 wt % solution at early bloom. This type of single treatments did control plant height although it was noticed that plant yields were occasionally reduced particularly if the plant was stressed during or after the application.

Since 1987, the trend has been to apply mepiquat chloride in a series of applications each having a lower dose than the single dose application. The first treatment occurs at match head square with a second treatment 7–14 days thereafter. Both treatments are made at a rate within the range from about 0–8 ounces of 4.2 wt % solution per acre with the specific application rate depending on whether the cotton plant was exhibiting signs of being stressed (no application), moderate growth (about 2 ounces of solution per acre), or vigorous growth (about 4 ounces of solution per acre). Thereafter, two additional treatments at 7–14 day intervals may be used with application rates extending up to about 8 ounces of 4.2 wt % mepiquat chloride solution with the specific application rate dependent on the amount of vegetative growth in the field. Further experimentation by individual growers has resulted in a wide variety of multiple application rates.

It would be desirable if the use of mepiquat chloride could be integrated into a system of treatment that would increase plant tissue mass in the roots, stems, and leaves to provide higher levels of nutrient transfer while, at the same time, restricting vegetative growth to enhance fruit production.

SUMMARY OF THE INVENTION

It is an objective of the present invention to provide a composition and method of use therefore to increase the uptake of applied agriculturally active ingredients as well as the intraplant transport thereof.

It is a further objective of the invention to provide a composition and method for its use on fruit-producing plants and seeds that increases the number of fruiting sites on treated plants with the goal of providing increased yields of fruit.

It is another objective of the invention to provide a composition and method for its use in which treated plants grow in a more healthy condition.

In accordance with these and other objectives of the invention that will become apparent from the description herein, a composition according to the invention comprises: (a) an agriculturally effective active ingredient comprising any of a plant growth regulating agent, a systemic fungicide, a systemic insecticide, or a systemic herbicide; and (b) a transport enhancer consisting essentially of B. subtilis (cells, cultures, or suspensions thereof) in an amount sufficient to enhance the effectiveness of said active ingredient. Preferably, the transport enhancer is free of plant growth hormones when used in combination with plant growth regulating agents, like mepiquat chloride, that suppress plant growth hormones.

Compositions according to the present invention improve the efficacy of the applied agriculturally active ingredient. The same amount of active material that is conventionally applied will be more effective. Lower levels of active ingredient can be used to achieve the same effect as the higher conventional application rate. In addition, plants that have treated with compositions according to the invention are healthier with the attendant benefit of being more resistant to disease or other stress as well as exhibiting higher numbers of fruiting sites and increased yields.

DETAILED DESCRIPTION

The invention provides a method for treating fruit-producing plants with a composition containing a transport enhancer consisting essentially of B. subtilis in an amount sufficient to enhance the effectiveness of an agriculturally effective active ingredient applied simultaneously, before, or after application of the transport enhancer. The increased effectiveness can be used to reduce the amount of applied agriculturally effective active ingredient or, when the active ingredient is applied at the same rate, the B. subtilis increases the effectiveness of the applied agriculturally effective active ingredient. Such increased effectiveness is useful for controlling weeds that are otherwise difficult to control with regular or systemic herbicides, for controlling insect populations with less systemic insecticide, and for treating fungus growth with lower levels of systemic fungicide.

Bacillus subtilis is a naturally occurring soil saprophyte found throughout the world. For compositions according to the invention, B. subtilis can be used in the form of cells, spores, cultures, or suspensions thereof and added to a spray tank or distribution reservoir as a stable, aqueous concentrate solution exhibiting an equivalent spore concentration within the range from about 300,000 colony forming units per milliliter (CFU/ml) to about 1.5 million CFU/ml, preferably about 1 million to about 1.2 million CFU/ml. Optionally and in a preferred embodiment, the spray tank will also contain at least one agriculturally effective active ingredient that is made from one or more plant growth regulating agents or systemically acting agents (e.g., fungicides, insecticides, or herbicides).

The specific dilution and B. subtilis application rate will depend on the method by which the solution is to be applied to the plant surfaces. For example, aerial spraying will employ a different dilution rate and application quantity than boom spraying or the use of manual sprayers. Preferably, the concentrated B. subtilis solution is applied to plant foliage at a rate within the range from about $0.1 \times 10^{10}$ CFU/acre to about $10 \times 10^{10}$ CFU/acre, preferably within the range from about $0.5 \times 10^{10}$ CFU/acre (0.5 fl. oz./acre of concentrate) to about $8 \times 10^{10}$ CFU/acre (2 fl. oz./acre of concentrate). Conventional equipment can be used for the application. If desired, the B. subtilis can be mixed with other treatments and applied simultaneously or can be applied in a discrete treatment step. Foliar application is the preferred method for increasing the number of fruiting sites on fruit-producing plants.

The concentrate can also be used to formulate a ready-to-use, packaged mixture of growth regulating agents and bacillus. So prepared, the B. subtilis suspension is diluted to an amount within the range from about 150,000 CFU/ml to about 600,000 CFU/ml and stored at a pH of less than 7. If necessary, any of the conventional acidifying agents or buffers (preferably food grade or those classified as "Generally Regarded As Safe" by the U.S. Environmental Protection Agency) may be used to maintain a suitable acidic pH to ensure storage stability. Under such acidic conditions, the spores remain stable and exhibit good storage stability. When diluted for use and following application, the pH of the solution will raise to greater than 7 thereby causing the B. subtilis suspension to become a live, vegetative colony. The bacillus will thereby reproduce on the treated plant surfaces and facilitate transport or translocation of the co-applied plant growth regulating agent.

For the invention, virtually any strain of B. subtilis that promotes the formation of fruiting sites in fruit producing plants can be used in accordance with the present invention. In the 1992 edition of the American Type Culture Collection, 182 different strains of B. subtilis are listed and incorporated herein by reference. Preferred strains for use in the present invention include GB03 and BP01 (ATCC Designation 55675).

Previously, B. subtilis GB03 was recognized as a biological fungicide and commercially used as a seed treatment under the names KODIAK™ HB or GUS 2000™ by Gustafson, Inc., Plano, Tex. 75093 (EPA Reg. No. 7501-146). This product is available as a 2.75% powder formulation containing not less than $5.5 \times 10^{10}$ viable spores per gram and is to be applied at a rate ranging from 2–4 ounces per 100 pounds of seed. The use directions indicate that the product is to be used for treatment of crop seeds only. The bacteria is said to colonize the developing root systems and compete with disease organisms that would attack the roots. Foliar application is not listed.

Plants that can be treated by the present invention include virtually any plant that produces fruiting sites from which fruit will grow. Such plants preferably include any of the raw agricultural commodity and especially cotton, soybeans, peanuts, grapes, apples, citrus (e.g., lemons, limes, oranges, grapefruit), berries (e.g., strawberries, blackberries, raspberries), tubers (e.g., potatoes, sweet potatoes), corn, cereal grains (e.g., wheat, rice, rye), tomatoes, onions, cucurbits (e.g., watermelon, cucumbers, and cantaloupes).

The B. subtilis can be applied as a discrete treatment or simultaneously with a variety of other agriculturally effective active ingredients. Useful agriculturally effective active ingredients include plant growth regulators, systemic fungicides, systemic insecticides, and systemic herbicides. Preferably, the composition is a combination of a plant growth regulating agent and a transportation enhancer consisting essentially of *B. subtilis* in an amount of at least $0.1\times10^{10}$ CFU/acre.

Plant growth regulators that can be used include plant growth hormones such as at least one of the 84 identified gibberillins with $CA_3$, $GA_4$, $GA_5$, $CA_7$ and $GA_9$ being preferred; cytokinins (e.g., zeatin, kinetin, benzyladenine, dihydrozeatin, and isopentenyl adenine); auxins (e.g., indolacetic acid (IAA), indolebutyric acid (IBA), and naphthalenacetic acid (NAA)); sodium ortho-nitrophenolate; sodium para-nitrophenolate; sodium 5-nitro-guaicolate; and polyhydroxycarboxylic acids of 2, 4, 5, and 6 carbon structures; ethephon; chlormequat chloride; mepiquat chloride; and fertilizers. Such plant growth regulators affect and alter plant metabolic processes to enhance or retard plant growth. All such agents can be used according to the application rates and timing specified by the manufacturer on the product label. Suitable systemic agents that will benefit from enhanced plant uptake, transport, and process assimilation include the systemic pesticides and systemic fungicides.

Systemic agents for plants that benefit from the present invention include, inter alia, aldicarb, acephate, carbofuran, dimethoate, phorate, and terbufos. Systemic fungicides that will benefit from the mixtures of the invention include tridemorph, metalaxyl, iprodione, fosetyl-aluminum, thiophanate, benomyl, triadimefon, carboxin, oxycarboxin, carbendazim, thiabendazole, thiophanate, ethirimol, bupirimate, and dimethirimol. Herbicides that will benefit from the invention include the triazines (e.g., atrazine), the ureas, glyphosate, sulfosate, glyfosinate, and sethoxydim.

It should be noted that formulations according to the present invention should not include combinations of materials that attempt to act in a contradictory fashion on the plant metabolism. For example, mepiquat chloride is commonly used on cotton foliage to suppress plant growth hormones and stunt the vegetative growth of the plant. A formulation would not be prepared that included plant growth hormones because the effects of the mepiquat chloride and the growth hormones would place inconsistent demands on the plant metabolism, reduce the efficacy of the mepiquat chloride, and lead to inconsistent results.

In a particularly preferred embodiment, a gibberellin-free transport enhancer containing *B. subtilis* is applied to the foliage of cotton plants at the same time the plants are treated with mepiquat chloride. An aqueous tank mixture containing *B. subtilis* and mepiquat chloride is a convenient method for simultaneously applying the components.

While not wishing to be bound by any particular theory of operation and with respect to the combined use of *B. subtilis* and mepiquat chloride on cotton, the *B. subtilis* appears to be specifically affecting the plant growth mechanism to increase the retention of bolls on fruiting sites 1 and 2 and increases the number of bolls overall by producing and retaining fruiting sites on normally vegetative branches.

Mepiquat chloride is used at the application rates and during the conventional stages of cotton plant growth. Conventionally applied rates of mepiquat chloride are up to about 60 g/acre (25 g/acre) or about 1–16 ounces per acre with individual application rates falling within the range from about 2.5 g/acre (1.0 g/hectare) for a 2 ounce/acre application of 4.2 wt % solution to 10 g/acre (4.1 g/hectare) for an 8 ounce/acre application of the same 4.2 wt % solution. If mepiquat chloride of higher or lower purity and/or activity is used, the specific application rate should be adjusted up or down according to the change in conventional mepiquat chloride activity.

EXAMPLES

Example 1

An aqueous mixture of 4.2 wt % mepiquat chloride and 560,000 CFU/ml bacillus BP01 (ATCC Designation 55675) was prepared in a 1:1 volumetric ratio. This solution was applied by conventional sprayer in four applications to the foliage of growing cotton plants in test areas of fields A (10 of 50 acres in Mississippi) and B (8 of 60 acres in Tennessee). Field A was treated with one dose at the rate of 4 fluid ounces per acre followed in five weeks by a treatment at the rate of 8 fluid ounces per acre.

Field B received a different treatment regiment. The first three applications in Field B were at the rate of 4 fluid ounces per acre. (The first and second were 24 days apart. The second and third were at 6 days apart). The final application in Field B was at the rate of 8 fluid ounces per acre 11 days later. In all cases, the control fields were treated with the same rate of only mepiquat chloride.

After treatment, sampling in Fields A and B was conducted by hand of representative rows. All known biases were placed in favor of the control treatment with only mepiquat chloride.

In Fields A and B, beginning and final plant heights of the treated cotton plants was measured. The total plant heights of the control fields was comparable to those treated according to the invention. See, Table 1.

TABLE 1

| Field | Beginning Height (in.) | Final height (in.) |
|---|---|---|
| A - Control | 293 | 601 |
| A - Treated | 291 | 597 |
| B - Control | 338 | 580 |
| B - Treated | 334 | 636 |

During the growing season, the differences between the control and treated plants were readily observed. When the young plants contained only squares in the first month of fruiting, an unusually high number and size of additional fruiting branches were seen where the primary fruiting branch exits the main stem. Many were as large or almost as large as the primary fruiting branch and contained fruit prior to first bloom. Extra fruit was also observed at the intersection of the fruiting branches and main stem.

As the bloom extended up the plant and only bolls or missing sites were found below the bloom, an unexpected amount of back fruiting was also observed. Double fruiting was observed in squares, blooms, small bolls, and "now open bolls" (rare). Although double fruiting occurred in both the control and treated plants, the instances were higher in the treated plants.

About 3–4 weeks before the end of the growing period, the plants were inspected for the number of fruiting sites, the number of bolls on nodes 1 and 2, as well as the type of boll. Table 2 reports the results of that inspection.

TABLE 2

| Field | Sites | Bolls | % | Open Bolls | Open + Green | Other Bolls |
|---|---|---|---|---|---|---|
| A - Control | 240 | 115 | 48 | 73 | 270 | 25 |
| A - Treated | 292 | 155 | 53 | 173 | 359 | 103 |
| B - Control | 344 | 207 | 60 | — | — | 81 |
| B - Treated | 366 | 234 | 64 | — | — | 163 |

In Field B and at the end of the test period, 20 plants were inspected. The plants were at cut-out. There were no open bolls in the control group and only 7 in the treated group. The younger fruit, however, were larger and older for the treated plants compared to the control plants. This indicates that the treated plants were growing at a faster and more favorable rate. The treated plants had a total of 265 bolls compared to 238 bolls for the control group, an improvement of 11%.

The treated plants also exhibited an increase in the number of fruit on the vegetative branches in the ratio of 88:51, an increase of about 73%. The treated plants also produced an increase in other fruit, i.e., those on fruiting branch positions 3 and wider, at the ratio of 86:50 (72% increase). The estimated weight (seed cotton) of the fruit from the 20 plants was also higher in the treated plants, 1796 g. v. 1456 g. (23% increase).

The extra fruit on the plants brought an expectation that the additional plant parts and young fruit would be a drain on the plant's system. Bolls would open sooner, but would adversely affect yield. This expectation was not realized. The treated plants grew at a faster rate and in a more healthy condition than the control.

To reduce bias, all lint was then harvested by hand from the test fields including unfluffed lint from partially opened bolls. Such unfluffed lint are usually from bolls that never opened correctly and are low on the plant or from bolls just opening that are high on the plant. Table 3 reports the weight of seed cotton and the number of green bolls per 10 foot of row in the treated and control fields.

TABLE 3

| Field | Seed cotton (g.) | Number of Green Bolls |
| --- | --- | --- |
| A - Control | 5322 | 97 |
| A - Treated | 6287 | 0 |
| B - Control | 4532 | 175 |
| B - Treated | 5058 | 42 |

The test results show that the combination of mepiquat chloride applied simultaneously with a transport enhancer containing ATCC 55675 according to the invention produces higher cotton yields and healthier plants than use of mepiquat chloride alone.

Example 2

ATCC 55675 was used in combination with a widely used herbicide, atrazine, to determine whether the ATCC 55675 would affect control over weeds that are recognized as difficult to kill with triazines. Atrazine is used to provide season-long control in corn, sorghum, and other crops at a suggested rate of 2 pounds active ingredient per acre. At sufficiently high rates, such as those used in this example, atrazine is recognized for its ability to provide nonselective weed control.

In sandy soil, three replicates of each test were performed in 12 ft.×25 ft. plots using a randomized complete block pattern. The weeds were 2–6 inches (5–15 cm) in height at the time of treatment. Atrazine was applied from aqueous solution at rates equivalent to either 1 or 2 pounds of active ingredient per acre. ATCC 55675 concentrate was added to the atrazine in an amount equivalent to either 0.5 or 1 fluid ounce per acre (0.5–1×10$^{10}$ CFU per acre). For comparison, crop oil concentrate (about 85% paraffinic oil and about 17% surfactant) was used as is conventional with triazine herbicides to increase their efficacy. Tables 4–8 report the degree of control for Florida Pusley (Table 4), Bull Grass (Table 5), Bermuda grass (Table 6), Dog Fennel (Table 7), and Primrose (Table 8).

TABLE 4

Florida Pusley

| | % Control After Treatment | | | |
| --- | --- | --- | --- | --- |
| Treatment | 4 days | 9 days | 16 days | 23 days |
| Control | 0 | 0 | 0 | 0 |
| Atrazine (1 lb.) | 3 | 33 | 42 | 45 |
| Atrazine (2 lb.) | 17 | 57 | 72 | 83 |
| Atrazine (1 lb) + crop oil conc. (1 gal.) | 28 | 62 | 68 | 68 |
| Atrazine (1 lb) + 0.5 oz. ATCC 55675 | 27 | 43 | 60 | 60 |
| Atrazine (1 lb) + 1 oz. ATCC 55675 | 22 | 53 | 65 | 67 |

TABLE 5

Bull Grass

| | % Control After Treatment | | | |
| --- | --- | --- | --- | --- |
| Treatment | 4 days | 9 days | 16 days | 23 days |
| Control | 0 | 0 | 0 | 0 |
| Atrazine (1 lb.) | 10 | 40 | 40 | 55 |
| Atrazine (2 lb.) | 25 | 70 | 80 | 90 |
| Atrazine (1 lb) + crop oil conc. (1 gal.) | 25 | 40 | 65 | 60 |
| Atrazine (1 lb) + 0.5 oz. ATCC 55675 | 35 | 40 | 55 | 63 |
| Atrazine (1 lb) + 1 oz. ATCC 55675 | 30 | 60 | 80 | 90 |

TABLE 6

Bermuda grass

| | % Control After Treatment | | | |
| --- | --- | --- | --- | --- |
| Treatment | 4 days | 9 days | 16 days | 23 days |
| Control | 0 | 0 | 0 | 0 |
| Atrazine (1 lb.) | 0 | 10 | 15 | 15 |
| Atrazine (2 lb.) | 8 | 15 | 22 | 27 |
| Atrazine (1 lb) + crop oil conc. (1 gal.) | 25 | 27 | 30 | 43 |
| Atrazine (1 lb) + 0.5 oz. ATCC 55675 | 7 | 20 | 37 | 68 |
| Atrazine (1 lb) + 1 oz. ATCC 55675 | 10 | 23 | 53 | 63 |

TABLE 7

Dog Fennel

| | % Control After Treatment | | | |
| --- | --- | --- | --- | --- |
| Treatment | 4 days | 9 days | 16 days | 23 days |
| Control | 0 | 0 | 0 | 0 |
| Atrazine (1 lb.) | 15 | 40 | 55 | 60 |
| Atrazine (2 lb.) | 17 | 55 | 70 | 95 |
| Atrazine (1 lb) + crop oil conc. (1 gal.) | 25 | 75 | 93 | 98 |
| Atrazine (1 lb) + 0.5 oz. ATCC 55675 | 33 | 88 | 96 | 99 |
| Atrazine (1 lb) + 1 oz. ATCC 55675 | 30 | 90 | 97 | 100 |

TABLE 8

Primrose

| Treatment | % Control After Treatment | | | |
|---|---|---|---|---|
| | 4 days | 9 days | 16 days | 23 days |
| Control | 0 | 0 | 0 | 0 |
| Atrazine (1 lb.) | 10 | 40 | 50 | 60 |
| Atrazine (2 lb.) | 30 | 65 | 70 | 80 |
| Atrazine (1 lb) + crop oil conc. (1 gal.) | 20 | 83 | 88 | 93 |
| Atrazine (1 lb) + 0.5 oz. ATCC 55675 | 20 | 60 | 72 | 88 |
| Atrazine (1 lb) + 1 oz. ATCC 55675 | 23 | 70 | 65 | 80 |

From Tables 4–8, it can be seen that ATCC 55675 generally improved the effectiveness of the atrazine at 23 days after treatment. The control rate at 1 lb. of atrazine with the bacillus was better than the control rate of 2 lb. atrazine for Bermuda grass, Dog Fennel, and Primrose, and the two treatments had the same control rate for Bull Grass. Only with Florida Pusley and 1 lb/acre of atrazine with ATCC 55675 was the control rate reduced relative to the 2 lb/acre treatment with atrazine.

Similarly, the ATCC 55675 also improved the control rate of atrazine relative to a mixture of atrazine and crop oil concentrate in all weeds except for Florida Pusley and Primrose. Such an improvement suggests that the bacillus is not acting as a surfactant, but is enhancing effectiveness by either or both of the metabolic activity or translocation characteristics of the co-applied agent.

The preceding are intended solely for purposes of illustrating the invention and are not intended to act as limitations on the scope of the appended claims.

We claim:

1. A composition useful for enhanced effectiveness of an agriculturally effective active ingredient, said composition consisting essentially of:

an agriculturally effective active ingredient comprising a plant growth regulating agent, systemic fungicide, systemic insecticide, or herbicide; and a transport enhancer of ATCC 55675 cells, spores, cultures or suspensions thereof in an amount sufficient to enhance the effectiveness of said agriculturally effective active ingredient.

2. A composition as in claim 1 wherein said plant growth regulating agent comprises mepiquat chloride.

3. A composition as in claim 1 wherein said plant growth regulating agent comprises chlormequat chloride.

4. A composition as in claim 1 wherein said plant growth regulating agent comprises ethephon.

5. A composition as in claim 1 wherein said plant growth regulating agent comprises a triazine herbicide.

6. A composition as in claim 5 wherein said plant growth regulating agent comprises atrazine.

7. A composition as in claim 1 wherein said transportation enhancer is present in an amount within the range from about 150,000 CFU/ml to about 600,000 CFU/ml.

8. A composition as in claim 1 wherein said composition exhibits a pH of greater than 7.

9. A method for increasing the number of fruiting sites on fruit-producing plants by a process which comprises the steps of:

applying to plant foliage a composition consisting essentially of: a transport enhancer consisting essentially of ATCC 55675.

10. A method as in claim 9 wherein the applying step comprises:

applying said transport enhancer to said plant foliage at a rate within the range from about $0.1\times10^{10}$ CFU/acre to about $10\times10^{10}$ CFU/acre.

11. A method as in claim 9 wherein the applying step comprises:

applying said transport enhancer to said plant foliage at a rate within the range from about $0.5\times10^{10}$ CFU/acre to about $8\times10^{10}$ CFU/acre.

12. A method as in claim 9 wherein the applying step comprises applying said bacillus from a suspension of 150,000–600,000 CFU/ml at a rate of at least $0.1\times10^{10}$ CFU/acre.

13. A method for enhancing the effectiveness of a co-applied agriculturally effective active ingredient by a process comprising:

applying to plant foliage a composition consisting essentially of: (a) an agriculturally effective active ingredient comprising a plant growth regulating agent, systemic insecticide, or herbicide; and (b) a transport enhancer of ATCC 55675 cells, spores, cultures or suspensions thereof in an amount sufficient to enhance the effectiveness of said agriculturally effective active ingredient.

14. A method as in claim 13 wherein the applying step comprises:

applying said composition wherein said plant growth regulating agent comprises chlormequat chloride.

15. A method as in claim 13 wherein the applying step comprises:

applying said composition wherein said plant growth regulating agent comprises ethephon.

16. A method as in claim 13 wherein the applying step comprises:

applying said composition wherein said plant growth regulating agent comprises mepiquat chloride and said composition is free of plant growth hormones.

17. A method as in claim 16 wherein the applying step comprises:

applying said transport enhancer and said growth regulating agent to cotton plant foliage simultaneously.

18. A method as in claim 17 wherein the applying step comprises applying said bacillus from a suspension of 150,000–600,000 CFU/ml at a rate of at least $0.1\times10^{10}$ CFU/acre.

* * * * *